United States Patent
Romero

(10) Patent No.: US 8,282,947 B2
(45) Date of Patent: Oct. 9, 2012

(54) LOW VISCOSITY, UNSTABLE WATER-IN-SILICONE EMULSION COSMETIC COMPOSITIONS AND METHODS OF USE THEREOF

(75) Inventor: Cheryl L. Romero, Brampton (CA)

(73) Assignee: Make-up Art Cosmetics, Inc., New York, NY (US)

( * ) Notice: Subject to any disclaimer, the term of this patent is extended or adjusted under 35 U.S.C. 154(b) by 1193 days.

(21) Appl. No.: 11/426,036

(22) Filed: Jun. 23, 2006

(65) Prior Publication Data

US 2007/0009446 A1      Jan. 11, 2007

Related U.S. Application Data

(60) Provisional application No. 60/698,427, filed on Jul. 11, 2005.

(51) Int. Cl.
| | | |
|---|---|---|
| *A61K 8/02* | (2006.01) | |
| *A61K 9/00* | (2006.01) | |
| *A61K 8/00* | (2006.01) | |
| *A61Q 5/12* | (2006.01) | |
| *A61Q 5/06* | (2006.01) | |

(52) U.S. Cl. ...... 424/401; 424/47; 424/70.1; 424/70.12; 424/70.16

(58) Field of Classification Search ............ 424/401, 424/47, 70.16, 70.12
See application file for complete search history.

(56) References Cited

U.S. PATENT DOCUMENTS

| | | |
|---|---|---|
| 3,985,587 A | 10/1976 | Chocy, Jr. |
| 4,309,119 A | 1/1982 | Wittersheim |
| 4,689,168 A | 8/1987 | Requejo |
| 4,742,963 A | 5/1988 | Marvaldi |
| 5,162,410 A | 11/1992 | Sweet |
| 5,330,747 A | 7/1994 | Krzysik |
| 5,451,610 A | 9/1995 | Krzysik |
| 5,468,477 A | 11/1995 | Kumar et al. |
| 5,665,368 A | 9/1997 | Lentini et al. |
| 5,725,845 A | 3/1998 | Krog et al. |
| 5,800,816 A | 9/1998 | Brieva et al. |
| 6,030,523 A | 2/2000 | Varadaraj et al. |
| 6,149,900 A | 11/2000 | Afriat et al. |
| 6,159,480 A * | 12/2000 | Tseng et al. ............. 424/401 |
| 6,162,421 A * | 12/2000 | Ordino et al. ............. 424/64 |
| 6,284,802 B1 * | 9/2001 | Bissett et al. ............ 514/739 |
| 6,299,890 B1 | 10/2001 | Russ et al. |
| 6,458,390 B1 | 10/2002 | Manelski et al. |
| 6,531,142 B1 | 3/2003 | Rabe et al. |
| 6,589,541 B2 | 7/2003 | Halston et al. |
| 6,667,046 B2 * | 12/2003 | Leo et al. .................. 424/401 |
| 6,726,900 B2 | 4/2004 | Scancarella et al. |
| 6,818,599 B2 | 11/2004 | Gonzalez et al. |
| 2004/0067483 A1 | 4/2004 | Zhao et al. |
| 2004/0086474 A1 | 5/2004 | Rabe et al. |

FOREIGN PATENT DOCUMENTS

| | | |
|---|---|---|
| CA | 2431898 A1 | 2/2002 |
| JP | 2001-58923 | 3/2001 |
| JP | 2001-058923 | 3/2001 |
| JP | 2001-328931 | 11/2001 |
| WO | WO00/72817 | 12/2000 |

OTHER PUBLICATIONS

PCT International Search Report; International Application No. PCT/US06/025630; Completion Date: Nov. 10, 2006; Date of Mailing: Nov. 10, 2006.
PCT Written Opinion of the International Searching Authority, or the Declaration; International Application No. PCT/US06/025630; Completion Date: Nov. 10, 2006; Mailing Date: Nov. 10, 2006.
Fingas et al.: "Studies of the formation process of water-in-oil emulsions", Marine Pollution Bulletin, vol. 47, 2003, pp. 369-396, DOI: doi:10.1016/S0025-326X(03)00212-1, p. 372, col. 2, line 5-line 11.
Supplemental European Search Report; EP06774371; Completion Date: Apr. 14, 2011; Date of Mailing: May 10, 2011.

* cited by examiner

*Primary Examiner* — Sreeni Padmanabhan
*Assistant Examiner* — Jody Karol
(74) *Attorney, Agent, or Firm* — Julie Blackburn

(57) ABSTRACT

A low viscosity, unstable water-in-silicone emulsion cosmetic composition stabilized upon agitation comprising a volatile solvent, a water phase dispersed within the composition, at least one silicone film-forming polymer and at least one emulsifier, and methods of use thereof as a sprayable composition.

16 Claims, No Drawings

LOW VISCOSITY, UNSTABLE WATER-IN-SILICONE EMULSION COSMETIC COMPOSITIONS AND METHODS OF USE THEREOF

This application claims priority of U.S. No. 60/698,427, filed Jul. 11, 2005.

FIELD OF THE INVENTION

The present invention relates to skin care cosmetic compositions and methods. In particular, the present invention relates to novel low viscosity, unstable water-in-silicone cosmetic compositions and methods of use thereof.

BACKGROUND OF THE INVENTION

Applying makeup to the skin and face is a daily ritual for many. Makeup may be applied to cover defects in the skin, to conceal variations in color, to hide scars or blemishes, or to accent certain of the wearer's features. This process of concealing imperfections and accentuating wearers' features serves to increase wearers' self-confidence, thereby facilitating social interactions and increasing their quality of life.

Each of the various forms of makeup is applied with specialized tools. For example, it is common to apply the makeup by hand, from tubes, with brushes, sponges, or with cosmetic pencils. However, the application of the makeup by hand leads to human error. For example, when applying foundation, eye shadow or other color cosmetic, if the composition is too thick, it may be difficult to evenly apply onto the skin without leaving streaking marks.

In order to achieve a color or a look that will last all day, the wearer typically is forced to apply more makeup than is desired in the morning. This allows a portion of the makeup to wear off throughout the day, without the need to constantly reapply the products. If makeup had a longer wearing-life, then the user would be able to apply a smaller amount and still have the effects of makeup later in the day. Over-application, which is necessary to have the appearance of wearing makeup throughout the entire day without reapplication would then be unnecessary.

Another common problem with many types of makeup is that it is detrimental to the skin. Many types of makeup have a tendency to clog the skin's pores and facilitate the formation of pimples. Additionally, components of the makeup, as well as the makeup removers that are necessary with many non-water-based cosmetics, tend to remove the skin's natural moisturizers and dry the skin.

To overcome many of the problems described above, it is known in the art to apply makeup through an airbrush technique using devices that spray fine droplets of the makeup onto the skin. See for example, U.S. Pat. No. 4,742,963, entitled "Aerosol Airbrush" and U.S. Pat. No. 4,309,119, entitled "Applicator Device for Cosmetic Preparations". Such devices, however, are generally only suitable for spraying water-soluble compounds. Water-soluble compounds are not water resistant and tend to rub or wear off easily. Compositions that are not water-based, however, are often too viscous to use airbrush techniques for application onto the skin. For instance, silicone-based makeup cosmetic compositions in emulsion form can be highly viscous due to the type and amount of ingredients needed to maintain a stable composition. More specifically, many silicone-based emulsion compositions require the use of heavy emulsifiers to create a thickness that will hold the composition in a stable emulsion form. With such high viscosity, however, the compositions are difficult to apply evenly on the face without streaking or smearing and are not suitable for application using airbrush techniques.

Therefore, there remains a need for personal makeup compositions that may be applied by the user evenly, quickly and accurately while exhibiting water resistance and long-wearing properties and avoiding problems associated with viscous compositions.

SUMMARY OF THE INVENTION

The present invention comprises a low viscosity, unstable water-in-silicone emulsion cosmetic composition stabilized upon agitation comprising a volatile solvent, a water phase dispersed within the composition, at least one silicone film-forming polymer and at least one emulsifier.

The present invention further comprises a kit and system for providing a sprayable make-up composition comprising a spray gun and a composition as described above.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

"Low viscosity" means that the composition in totality has a viscosity in the range of up to 1200 cps (centipoise), specifically between 200 to 1200 cps. The Viscometer used is preferably Brookfield LV, specifically LV3/30/1 (the 3 indicates spindle type, the speed is 30 rpm and the time is 1 minute). Centipoise is the measurement of absolute viscosity using a Viscometer. The viscometer measures the force needed to rotate the spindle in a fluid (sheer stress) at a known velocity (sheer rate). The viscosity is measured as the dial reading multiplied by the spindle multiplying factor (40) for the viscometer used. In the present invention, the dial readings are between 5 to 30, yielding 200 to 1200 cps.

"Unstable" means the water phase in the water in silicone emulsions partially coalesces such that the composition generally separates into visually distinct layers, the number of layers dependent upon the type and amount of components included within the composition. Generally speaking, and while specific components will be distributed in each layer, it is believed that the most dense components (e.g. metal oxide pigments) settle in the bottom layer while the less dense components are dispersed more within the middle and top layers.

Water-in-silicone emulsions usually require highly viscous emulsifiers to create a stable emulsion. The viscosity of the entire emulsion is therefore relatively high in relation to typical water-based emulsions. It is important to provide a stable emulsion to provide delivery of all of the components evenly onto the skin. For example, volatile solvents used as carriers in water-in-silicone emulsions will evaporate if not supported in a stable emulsion, therefore leading to transplant of higher amounts of the components carried in the solvent. In the present invention, it has been surprisingly found that a low-viscosity, unstable water-in-silicone emulsion cosmetic composition stabilized upon agitation is desirable over a stable water-in-silicone emulsion because it avoids the difficulties that two phase stable emulsions or suspensions may cause (as shown in Example 1 below), while delivering the components in a stable emulsion form onto the skin. Specifically, the present inventive composition is designed to be unstable so that the cosmetic benefits from the components (e.g., smooth skin feel, non-tacky composition, water-resistant) are not diluted through complete solubilization of the components, as may be the result in a stable emulsion. Instead, the unstable emulsion, through loose bonds holding the components together, allows the components to be better preserved in their original state while in the composition until the composition is stabilized during agitation. Since the components of an unstable emulsion will not be evenly distributed upon application, the present inventive is mechanically stabilized prior to application upon the skin to provide a more even delivery of such components onto the skin. The components therefore surprisingly retain more of their original characteristics and the applied composition does not streak, has resistance to water and has transfer resistant properties.

The present inventive composition comprises a low-viscosity, unstable water-in-silicone emulsion cosmetic composition stabilized upon agitation comprising a volatile solvent, a water phase dispersed therein, at least one silicone film-forming polymer and at least one emulsifier. By proper adjustment of the concentrations of the water phase constituents, the volatile solvent, the silicone film forming polymers and the emulsifiers, the present inventive composition is obtained in which the individual phases, when agitated/mixed, form an emulsion that, although short-lived upon application onto the skin due to the thinness of the layer and surface tensions of the composition, are sufficiently stable within a container/applicator so as to allow application of the composition over a period of time without repeated shaking of the container/applicator. In the preferred embodiment, the composition separates into at least three visually distinct layers in its unstable form, prior to mechanical agitation.

While specific components will be distributed in each phase, the water phase comprises water while the silicone phase comprises the film-forming silicone polymers, the volatile solvent and the emulsifiers. Additional components may appear in either phase, depending upon the affinity thereof. Agitation may be conducted externally by hand or mechanical means generally known to those skilled in the art, or through mechanical mixing means placed within an applicator/container, as is also well known to those skilled in the art.

The present inventive composition must have a viscosity between 200 to 1200 cps, preferably from 200 to 800 cps, and most preferably from 200 to 240 cps. Each of the components of the present invention may contribute to the viscosity of the final composition and therefore it is essential that the components are selected in a type and amount so as to not interfere with the low viscosity of the inventive composition.

Volatile Solvent

The volatile solvent is present such that it does not interfere with the low viscosity of the inventive composition. As used herein, "volatile" refers to substances with a significant amount of vapor pressure under ambient conditions, as is understood by those in the art. The volatile solvents for use herein will preferably have a flash point of up to 223 F for solvents with no greater than a 20 carbon chain. Preferably, the volatile solvents for use herein will be relatively odorless and safe for use on human skin. Suitable volatile carriers include $C_1$-$C_{20}$ hydrocarbons and mixtures thereof. Preferred volatile carriers are $C_1$-$C_{12}$ hydrocarbons. More specifically, the volatile carrier is selected from the group consisting of volatile dimethicone (i.e., having a flashpoint of between 26 F to 223 F), isododecane, isohexadecane, isoeicosane, isooctane, cyclomethicone and mixtures thereof. Most preferably, the volatile solvent is isododecane.

The volatile carrier is used in an amount of from 10% to 95%, preferably from 15% to 80%, and most preferably from 30% to 50%.

Water Phase

The water phase is dispersed within the volatile solvent when the composition is stabilized upon agitation and comprises water in the amount of from 0.001 to 45%, preferably from 1 to 20% and most preferably between 10 to 15%. In the unstable state, the water phase tends to mostly settle at the bottom of the composition and is therefore only partially dispersed within the volatile solvent. It is essential that the amount of water in the present inventive composition is controlled such that the viscosity of the composition does not exceed the range described hereinabove to maintain a low-viscosity composition.

Silicone Film-Forming Polymer

Any silicone film-forming polymer which does not interfere with the overall low-viscosity feature of the inventive composition may be used. Silicone polymers are known to form a film upon the skin upon application thereon and are known to those skilled in the art. In the present invention, the silicone film forming polymer is selected from the list consisting of dimethicone and siloxane derivatives. Specifically, a dimethicone or siloxane derivative is preferably a compound that is a reaction product between a silica dioxide, or derivatives thereof, and a silanol-endblocked polydiorganosiloxane fluid having a viscosity of from about 1,000 to about 200,000 cps. Any silica derivative can be used, provided it has sufficient hydroxy radical density to react with the silanol-endblocked diorganosiloxane. In a preferred embodiment, the derivatives are triorganosilyl-endblocked silica dioxide, reacted with a polydiorganosiloxane having a viscosity of about 10,000 to about 15,000 cps. The preferred compounds are non-flowable solids at room temperature, and have a viscosity well in excess of 10,000,000. Examples of the manufacture of these materials are found in U.S. Pat. No. 5,162,410, the contents of which are incorporated herein by reference. U.S. Pat. Nos. 5,330,747 and 5,541,610, suggests their use in certain personal care products. However, to the best of Applicants' knowledge, these materials have not been previously suggested for use in a low-viscosity, unstable water-in-silicone composition. Preferred film-forming polymers of the invention are available commercially from Dow Corning under the trade name BIO-PSA®. BIO-PSA® comes in two forms, standard and amine compatible, and are provided in a variety of solvents and resin-to-polymer ratios. Any of the BIO-PSA® materials is suitable for use in the present invention; however, preferred are the standard form adhesives, and particularly preferred is the BIO-PSA® identified by product number 7-4405, which has a resin-to-polymer ratio of 60/40 and an isododecane solvent, known as dimethicone/silylate isododecane. Also preferred is poly (dimethylsiloxane)-g-poly(isobutyl methacrylate) (sold under the Tradename Polysilicone-6®), isododecane/acrylate copolymer (sold under Tradename Giovarez® AC-5099M).

In the present invention, the film-forming polymers may be used alone or in combination to provide an enhanced smooth feel, while improving transfer resistance of the final composition. The film forming polymer is used in amount of from 1% to 60%, preferably from 2% to 20% and most preferably from 3% to 10%. It should be noted that the amount of the film forming polymer may be adjusted within the limits defined above and in relation to the other components of the present composition through routine experimentation such that the viscosity of the entire inventive composition does not exceed the parameters defined herein.

Emulsifier

The present composition further comprises an emulsifier that partially emulsifies the inventive composition. By the term "partially emulsify," it is meant that the composition does not remain in a stable two phase emulsion form without the aid of agitation of the total composition, as described hereinabove. Specifically, the emulsifier is used in an amount and viscosity range such that the emulsifier does not enable the emulsion to remain in a stable two phase system and instead the composition generally separates into visually distinct layers, the number of layers depending upon the type and amounts of the specific components included within the composition. As explained above, in a stable two phase system, the emulsifier contributes towards completely solubilizing/emulsifying components of the compositions such as a silicone polymer to create a stable water-in-silicone system. As a result, the properties of such silicone film forming polymers in their original state, such as transfer resistance and emolliency among others, may be diluted during transfer onto the skin. In the present invention, since the silicone polymer is not completely emulsified and instead is loosely held within several visually distinct layers of the present composition, the properties of the silicone polymer are more readily preserved. Stabilization of the inventive composition through agitation provides a delivery medium that is stable enough to deliver the silicone polymer to the skin uniformly with relation to the other components of the present invention. Therefore, the partial emulsification of the present invention contributes to the water resistance/transfer resistance of the composition upon application.

Other than oil-in-water emulsifiers, any emulsifier in combination or alone, that has a viscosity of between 4 cps to 1600 cps may be used, preferably between 100 cps to 700 cps. It should be noted that a person of ordinary skill in the art would adjust the viscosity in accordance with other ingredients such that the viscosity of the total composition does not exceed the amount specified herein, specifically a maximum viscosity of 1200 cps. The emulsifier of the present invention includes water-in-oil emulsifiers and silicone-based emulsifiers. The typical water-in-oil emulsifier has a HLB value of about 4 to about 6, as is well known in the art; however, this "rule" is also known to have numerous exceptions. Selection of suitable water-in-oil emulsifiers is well known in the formulation art. Particularly, the emulsifier is selected from the group consisting of a mixture of Cetyl PEG 10 Dimethicone and a mixture of Cetyl Dimethicone Copolyol, Polyglyceryl 4-Isostearate and Hexyl Laurate (sold under the Tradename ABIL WE-09).

The emulsifier is used in an amount of from 0.001% to 30%, preferably from 0.01% to 15%, and most preferably from 0.1% to 1%. It should be noted that the amount of the emulsifier may be adjusted within the limits defined above and in relation to the other components of the present composition through routine experimentation such that the viscosity of the entire inventive composition does not exceed the parameters defined herein.

Pigments

For color compositions, optionally at least one pigment may be added to the composition. The pigments generally fall within the water phase and settle into the bottom layer before agitation of the composition. The pigments may be any pigment known to persons of ordinary skill in the art and include but are not limited to the group consisting of bronzers, micas, iron oxides, carbon black, titanium dioxide, aluminum flakes, bronze flakes, coated mica, nickel flakes, tin flakes, silver flakes, copper flakes and dyes. Further examples can be found in the International Cosmetic Ingredient Dictionary, CTFA, Ninth Edition, 2003. Pigment Load in the present inventive composition is from 5% up to 25% to avoid thickening the final composition beyond the range specified hereinabove to maintain the low viscosity of the present inventive composition.

The compositions of the present invention can be formulated into a wide variety of product types, including creams, lotions and sprays. Preferred compositions are formulated into cosmetic sprays. These product forms may be used for a number of applications, including but not limited to make-up compositions/cosmetics, self-tanning compositions, sunscreen compositions and moisturizers. Any additional components required to formulate such products vary with product type and can be routinely chosen by one skilled in the art.

Other Components

The formulation also can comprise other components that may be chosen depending on the carrier and/or the intended use of the formulation, as long as the viscosity of the total composition is maintained within the range specified herein. Additional components include, but are not limited to antioxidants (such as BHT); chelating agents (such as disodium EDTA); preservatives (such as methyl paraben); fragrances (such as pinene); emollients (such as dimethicone and its derivatives, dioctyl malate, octyldodecyl/PPG-3 myristyl ether dimmer dilinoleate); humectants (such as glycerine, butylene glycol, capryl glycol/phenoxythanol/hexylene glycol); moisturizing agents (such as cholesterol, butylene glycol); skin conditioning agents (such as trisiloxane), optical diffusers (such as silica); sunscreens (such as octyl methoxycinnamate, titanium dioxide, zinc oxide, camphor derivatives, cinnamates, salicylates, benzophenones, triazines, PABA derivatives, diphenylacrylate derivatives, and dibenzoylmethane derivatives) and the like.

The compositions can also encompass one or more additional active components, and as such can be either cosmetic or pharmaceutical compositions in addition to color cosmetics, such as anti-aging and concentrations may be determined by one skilled in the art to determine effectiveness of product as discussed in the present invention. Such additional active components should also be selected so that the overall viscosity of the composition does not exceed the limitations defined hereinabove. Examples of useful actives include, but are not limited to, those that improve or eradicate age spots, keratoses and wrinkles, analgesics, anesthetics, anti-acne agents, antibacterials, antiyeast agents, antifungal agents, antiviral agents, antidermatitis agents, antipruritic agents, antiemetics, antihyperkeratolytic agents, anti-dry skin agents, antipsoriatic agents, antiseborrheic agents, antiaging agents, antiwrinkle agents, antihistamine agents, wound-healing agents, vitamins, corticosteroids, additional tanning agents or hormones. More specific examples of useful active agents include retinoids such as retinol, and esters, acids, and aldehydes thereof, ascorbic acid, and esters and metal salts thereof, tocopherol and esters and amide derivatives thereof, shark cartilage; milk proteins; alpha- or beta-hydroxy acids; DHEA and derivatives thereof; topical cardiovascular agents; clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, hydrocortisone, hydrocortisone 21-acetate, hydrocortisone 17-valerate, hydrocortisone 17-butyrate, betamethasone valerate, betamethasone diproprionate, triaminolone acetonide, fluocinonide, clobetasol, proprionate, benzoyl peroxide, crotamiton, propranol, promethazine, and mixtures thereof.

Particularly preferred embodiments of the present formulations are skin care formulas used as makeup compositions or color cosmetics.

Method of Making the Composition

The present inventive composition can be made by first placing a silicone film-forming polymer in a beaker. A volatile solvent is then added to the polymer. Once the mixture is uniform, then optionally, another silicone film-forming polymer may be added, depending on preference of feel for the resulting composition. An emulsifier is then added into the mixture and mixed until uniform.

Optionally, pigments and micronized pigments are placed in a smaller beaker with isodedecane and dimethicone copolyol for pigment dispersion and ball milled (additional isodedecane is used for rinse). Once checked with glass slides to ensure no undispersed pigments are found the small beaker contents are added to the main beaker. Mix until uniform approximately 5 minutes and then the silicas and anti-oxidants are added.

The dispersed water phase is made using water and any other desired optional ingredients for the water phase. Once the mixture is uniform, 10% of the total water phase is added to the silicone composition with use of a propeller. Once 10% of the water phase is added, the resulting composition is mixed for 5 minutes. The remainder of the water phase is then added for a total of 15 minutes. The resulting composition is mixed for 15 more minutes. The composition is then removed from the propeller and optionally a homogenizer is added for 5 minutes at 4.8 - 5.2 rpm.

Methods of Use

The present inventive compositions are particularly useful as products for methods of improving the look of skin with makeup, color compositions or self-tanning compositions as well as diminishing the look of lines and wrinkles on the skin.

Such methods comprise administering or topically applying to the skin a safe and effective amount of the composition of the present invention. The amounts of the components in the compositions will vary depending upon the level of coverage desired and the individual's skin type.

A preferred method of cosmetically or pharmaceutically treating the skin is via topical application of a safe and effective amount of the novel composition through an air pump system to provide an airbrush look upon application of the inventive composition onto the skin. The air pump system has an spray gun attached to an air compressor, whereby an amount of the composition may be poured into the gun and sprayed onto the desired area of skin. The spray gun may be any gun commercially available (such as Side Feed Gun ECL3500 IWATA ECLIPSE SBS SIDE FEED sold by Iwata). The model of the airbrush gun can have either a fixed cup with one orifice on top of the gun, two orifices on either side to accommodate either a removable side feed cup, or a side feed adapter to connect directly into the composition of the present invention. Depending upon the desired flow of the composition onto the skin, a person skilled in the art is capable of choosing the desired number of orifices and the type of spray gun to be used. It should be noted that the present inventive composition may also be applied through traditional methods such as the use of the user's hand, a sponge, or a brush.

It is suggested as an example that topical application range from about once per month to about once daily, preferably from about once every week to about twice per week, most preferably about once or twice a day. The composition is applied in an amount of from 0.001 g up to 20 g in the air pump, depending on the holding capacity of the pump. The amount of composition applied to the skin will vary depending upon coverage desired.

The following examples further illustrate the invention, but the invention is not limited thereto.

EXAMPLE 1

The inventive composition used in the examples is provided herein below. Optional ingredients such as pigments, emollients, antioxidants and skin conditioning agents are disclosed in the composition provided herein below.

TABLE 1

| Composition | | |
|---|---|---|
| TRADE NAME | CTFA NAME | PERCENT |
| PERMETHYL 99A | ISODODECANE | 25.82900 |
| SILICONEES PLUS POLYMER VS70 DRY | POLYSILICONE-6 | 6.000000 |
| LIQUIWAX POLYEFA | OCTYLDODECYL/PPG-3 MYRISTYL ETHER DIMER DILINOLEATE | 4.000000 |
| DC 7-4405 COSMETIC FLUID | DIMETHICONE SILYLATE/ISODODECANE | 5.500000 |
| DOW CORNING 200 FLUID, 5 CST | DIMETHICONE | 4.000000 |
| SILICONE HL88 | DIMETHICONE | 0.750000 |
| DOW CORNING 593 FLUID | DIMETHICONE/TRIMETHYLSILOXYSILICATE | 2.000000 |
| CERAPHYL 45 | DIOCTYL MALATE | 0.450000 |
| ABIL WE-09 | CETYL PEG/PPG-10/1 DIMETHICONE//POLYGLYCERYL-4 ISOSTEARATE/HEXYL LAURATE | 1.000000 |
| GRANSIL IDS GEL | POLYSILICONE-11/ISODODECANE | 10.00000 |
| DC 200 FLUID, 1 CST. | TRISILOXANE | 11.45000 |
| GRANSURF 77 | DIMETHICONE COPOYLOL | 1.000000 |
| CARDRE TITANIUM DIOXIDE AS R3435 | TITANIUM DIOXIDE/TRIETHOXYCAPRYLYLSILANE | 10.150000 |
| CARDRE YELLOW IRON OXIDE AS R2592 | IRON OXIDES/TRIETHOXYCAPRYLYLSILANE | 0.280000 |
| CARDRE RED IRON OXIDE AS 72591 | IRON OXIDES/TRIETHOXYCAPRYLYLSILANE | 0.050000 |
| CARDRE BLACK IRON OXIDE AS 72593 | IRON OXIDES/TRIETHOXYCAPRYLYLSILANE | 0.020000 |
| MSS-500/5H-SH | SILICA/METHICONE | 5.000000 |

TABLE 1-continued

Composition

| TRADE NAME | CTFA NAME | PERCENT |
|---|---|---|
| MSS-500W | SILICA | 1.100000 |
| VITAMIN A PALMITATE | CORN OIL/RETINYL PALMITATE | 0.010000 |
| VITAMIN E, U SP, FCC, CODE 60526 | TOCOPHERYL ACETATE | 0.010000 |
| ASCORBYL PALMITATE NF-FCC 60412 | ASCORBYL PALMITATE | 0.001000 |
| SODIUM CHLORIDE GRANULAR USP | SODIUM CHLORIDE | 0.350000 |
| DEIONIZED WATER | PURIFIED WATER | 9.000000 |
| 1,3 BUTYLENE GLYCOL | BUTYLENE GLYCOL | 1.050000 |
| DIOCIDE | CAPRYLYL GLYCOL/PHENOXYETHANOL/HEXYLENE GLYCOL | 1.000000 |

EXAMPLE 2

The present inventive composition described in Table 1, Example 1, above with the low-viscosity, unstable water-in-silicone emulsion resulting in three phases is compared to a water-in-silicone two phase emulsion and a suspension. The two phase emulsion comprises the composition in Table 2 below. The suspension comprises the composition of Table 1 without the emulsifier. The compositions are applied into an airbrush spray gun and applied onto the skin. Each composition is tested for viscosity and stability prior to application into the airbrush spray gun. The application onto the skin is then visually analyzed for coverage and feel. The two phase composition is provided in Table 2 below and the results of the tests are shown in Table 3 below.

TABLE 2

| INGREDIENT | PERCENT |
|---|---|
| WATER PURIFIED | 25.906 |
| CYCLOPENTASILOXANE | 23.200 |

TABLE 2-continued

| INGREDIENT | PERCENT |
|---|---|
| PHENYL TRIMETHICONE | 7.7000 |
| TITANIUM DIOXIDE | 7.08385 |
| BUTYLENE GLYCOL | 7.00000 |
| SILICA | 6.51200 |
| DIMETHICONE | 6.09000 |
| MICA | 5.55000 |
| BIS-PEG/PEG-14/14 DIMETHICONE | 2.55000 |
| MAGNESIUM SULFATE | 2.00000 |
| TITANIUM DIOXIDE | 1.94000 |
| TRIMETHYLSILOXYSILICATE | 1.75000 |
| PHENOXYETHANOL | 0.64400 |
| IRON OXIDES | 0.57915 |
| DISTEARDIMONIUM HECTORITE | 0.36000 |
| TRIETHOXYCAPRYLYLSILANE | 0.19000 |
| POLYGLYCERYL 4 ISOSTEARATE | 0.16700 |
| CETYL PEG/PPG10/DIMETHICONE | 0.16650 |
| HEXYL LAURATE | 0.16650 |
| LAURETH-7 | 0.15000 |
| PROPYLPARABEN | 0.10000 |
| TRIETHYL CITRATE | 0.10000 |

TABLE 3

INVENTIVE SYSTEM VS. 2-PHASE SYSTEM AND SUSPENSION

| Observations | Inventive System with multiple phases | 2-Phase System | Suspension |
|---|---|---|---|
| Stability | Becomes stable system upon agitation | Stable without agitation | Components separate out, Composition Doesn't Stabilize Upon Agitation |
| Airbrush Application | Sprayable through a gun | Not sprayable through a gun | Thickens over time, not sprayable through a gun |
| Effect Of Pigments | No Streaking Or Thickening Due To Coated Pigments | No Streaking Or Thickening Due To Coated Pigments | Composition streaks/settles when applied to skin/pigments cause additional thickening |
| Viscosity | Partially emulsified; Has Resistance to Water and Transfer Resistance Properties | Completely Emulsified; Highly Viscous, Has Water Resistance but not as Transfer Resistant As Multiple Phase System | No Resistance to Water, not Transfer Resistant |

As seen in Table 3 above, the present inventive system has a viscosity that is thin enough to pass through an airbrush for application while remaining unstable until agitation so as to provide water resistance and transfer resistance in comparison to the 2-phase system and the suspension.

EXAMPLE 2

Comparative Example of Emulsifiers

The control composition of Table 1 is tested with variations in emulsifiers. Emulsifier 1 is Cetyl PEG/PPG-10/1 Dimethicone/Polyglyceryl-4 Isostearate/Hexyl Laurate (Abil WE-09, emulsifier of the present invention), Emulsifier 2 is Cetyl PEG/PPG10/Dimethicone (Abil EM-90) and Emulsifier 3 is Cyclopentasiloxane (and) PEG/PPG-18/18 (DC5225C). Four samples are made with Composition A containing 1% Emulsifier 1 (the present inventive composition), Composition B containing 1% Emulsifier 1 and 6% Emulsifier 2, and Composition C containing 1% Emulsifier 1 and 15% Emulsifier 3.

TABLE 4

COMBINATIONS OF EMULSIFIERS IN THE SYSTEM

| INGREDIENTS | A CONTROL WITH 1% EMULSIFIER 1 | B CONTROL + 1% EMULSIFIER 1 AND 6% EMULSIFIER 2 | C CONTROL + 1% EMULSIFIER 1 AND 15% EMULSIFIER 3 |
|---|---|---|---|
| VISCOSITY LV/3/30/1 (FACTOR 40) (dial reading) | 6.0 | 18.5 | 16.7 |
| APPLICATION/ FEEL | Good Feel, good coverage on skin upon application | Draggy Feel due to high viscosity | Oily; Little Coverage |
| STABILITY | Separated - 2.6 cm, Stabilizes immediately upon agitation | Signs Of Separation - 0.6 cm. | Separated - 4.5 cm; Curdled; Doesn't stabilize upon agitation |

As seen from the results in Table 4 above, the present inventive composition with only 1% emulsifier yields an unstable, low viscosity emulsion which exhibits the desired properties of good feel, good coverage and stability upon agitation. In contrast, the Composition B with enough combination of emulsifiers to create a stable composition, does not provide the desired feel because of its high viscosity. Moreover, a different combination of emulsifiers in Composition C yields an unstable composition which does not stabilize upon agitation, does not evenly cover the skin and has an oily and thus undesirable feel.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A water-in-silicone emulsion cosmetic composition stabilized upon agitation comprising:
   from about 15% to about 80% by weight of a volatile solvent selected from the group consisting of volatile dimethicone, isododecane, isohexadecane, isoeicosane, isooctane, cyclomethicone and mixtures thereof;
   from about 1% to about 20% by weight of a water phase dispersed within the composition;
   from about 2% to about 20% by weight of at least one silicone film-forming polymer selected from the group consisting of dimethicone/silylate isododecane and poly (dimethylsiloxane)-g-poly(isobutyl methacrylate); and
   from about 0.01% to about 15% by weight of at least one emulsifier selected from the group consisting of water-in-oil emulsifiers, silicone-based emulsifiers, and mixtures thereof, wherein said emulsifier has a viscosity ranging from about 4 cps to about 1600 cps,
   wherein the emulsion has a viscosity ranging from about 200 cps to about 1200 cps, and wherein the emulsion cannot remain in a stable two phase system and instead separates into visually distinct layers without the aid of agitation.

2. The composition of claim 1 wherein the silicone film-forming polymer is dimethicone/silylate isododecane.

3. The composition of claim 1 wherein the emulsifier is selected from the group consisting of a mixture of Cetyl PEG/PPG-10/Dimethicone and a mixture of Cetyl Dimethicone Copolyol, Polyglyceryl 4-Isostearate and Hexyl Laurate.

4. The composition of claim 1 wherein the volatile solvent is isododecane.

5. A kit for providing a sprayable make-up composition comprising: a spray applicator; and a composition as described in claim 1.

6. The kit of claim 5 wherein the spray applicator comprises a spray gun attached to an air compressor.

7. The kit of claim 5 wherein the silicone film-foorming polymer is dimethicone/silylate isododecane.

8. The kit of claim 5 wherein the emulsifier is selected from the group consisting of a mixture of Cetyl PEG/PPG-10/ Dimethicone and a mixture of Cetyl Dimethicone Copolyol, Polyglyceryl 4-Isostearate and Hexyl Laurate.

9. The kit of claim 5 wherein the volatile solvent is isododecane.

10. A system for applying a skin care composition to human skin comprising: a water-in-silicone emulsion cosmetic composition according to claim 1; and an applicator for applying the composition to the skin.

11. The system of claim 10 wherein the silicone film-forming polymer is dimethicone/silylate isododecane.

12. The system of claim 10 wherein the emulsifier is selected from the group consisting of a mixture of Cetyl PEG/PPG-10/Dimethicone and a mixture of Cetyl Dimethicone Copolyol, Polyglyceryl 4-Isostearate and Hexyl Laurate.

13. The system of claim 10 wherein the volatile solvent is isododecane.

14. The system of claim 10 wherein the applicator is a spray gun.

15. A water-in-silicone emulsion cosmetic composition stabilized upon agitation comprising:
   from about 15% to about 80% by weight of isododecane;
   from about 1% to about 20% by weight of water dispersed within the composition;
   from about 2% to about 20% by weight of dimethicone/silylate isododecane; and
   from about 0.01% to about 15% by weight of at least one emulsifier selected from the group consistinng of a mixture of Cetyl PEG/PPG-10/Dimethicone and a mixture of Cetyl Dimethicone Copolyol, Polyglyceryl 4-Isostearate and Hexyl Laurate.

16. A system for applying a skin care composition to human skin comprising: a water-in-silicone emulsion cosmetic composition according to claim 15; and an applicator for applying the composition to the skin.

\* \* \* \* \*